United States Patent
Moriya et al.

(10) Patent No.: US 8,218,145 B2
(45) Date of Patent: *Jul. 10, 2012

(54) PARTICLE MONITOR SYSTEM AND SUBSTRATE PROCESSING APPARATUS

(75) Inventors: Tsuyoshi Moriya, Nirasaki (JP); Takashi Enomoto, Albany, NY (US)

(73) Assignee: Tokyo Electron Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/111,520

(22) Filed: May 19, 2011

(65) Prior Publication Data

US 2011/0216322 A1    Sep. 8, 2011

Related U.S. Application Data

(63) Continuation of application No. 12/015,156, filed on Jan. 16, 2008, now Pat. No. 7,969,572.

(60) Provisional application No. 60/911,676, filed on Apr. 13, 2007.

(30) Foreign Application Priority Data

Jan. 30, 2007   (JP) ................................. 2007-019888

(51) Int. Cl.
    *G01N 21/00*    (2006.01)

(52) U.S. Cl. ...................... 356/338; 356/335

(58) Field of Classification Search .......... 356/335–343
    See application file for complete search history.

(56) References Cited

U.S. PATENT DOCUMENTS

| 3,578,867 | A  | 5/1971  | Barrington |
| 4,739,177 | A  | 4/1988  | Borden |
| 5,481,357 | A  | 1/1996  | Ahsan et al. |
| 6,674,528 | B2 | 1/2004  | Adachi et al. |
| 6,947,136 | B2 | 9/2005  | Ortyn et al. |
| 7,145,653 | B1 | 12/2006 | Templeton et al. |
| 7,170,602 | B2 | 1/2007  | Saito et al. |

FOREIGN PATENT DOCUMENTS

| JP | 5-206235   | 8/1993 |
| JP | 6-124902   | 5/1994 |
| JP | 2000-124202 | 4/2000 |
| JP | 2004-186565 | 7/2004 |

OTHER PUBLICATIONS

Office Action mailed Nov. 16, 2010, in co-pending U.S. Appl. No. 12/015,156.
Office Action mailed Apr. 30, 2010, in co-pending U.S. Appl. No. 12/015,156.
Japanese Office Action issued Aug. 2, 2011, in Patent Application No. 2007-019888. (with partial English translation).

*Primary Examiner* — Layla Lauchman
(74) *Attorney, Agent, or Firm* — Oblon, Spivak, McClelland, Maier & Neustadt, L.L.P.

(57) ABSTRACT

A particle monitor system that can detect fine particles in a substrate processing apparatus. The substrate processing apparatus has a chamber in which a substrate is housed and subjected to processing, a dry pump that exhausts gas out of the chamber, and a bypass line that communicates the chamber and the dry pump together. The particle monitor system has a laser light oscillator that irradiates laser light toward a space in which the particles may be present, and a laser power measurement device that is disposed on an optical path of the laser light having passed through the space and measures the energy of the laser light.

16 Claims, 7 Drawing Sheets

PARTICLE MONITOR SYSTEM AND SUBSTRATE PROCESSING APPARATUS

CROSS-REFERENCE TO RELATED APPLICATIONS

This application is a continuation of and claims the benefit under 35 U.S.C.§120 to U.S. application Ser. No. 12/015,156, filed Jan. 16, 2008, the entire content of which is incorporated herein by reference. U.S. application Ser. No. 12/015,156 is a Non-Provisional of U.S. application Ser. No. 60/911,676 filed Apr. 13, 2007, and claims the benefit of priority under 35 U.S.C. §119 to Japanese Patent Application No. 2007-019888, filed on Jan. 30, 2007.

BACKGROUND OF THE INVENTION

1. Field of the Invention

The present invention relates to a particle monitor system and a substrate processing apparatus, and in particular to a particle monitor system that detects particles in a chamber or an exhaust pipe of a substrate processing apparatus.

2. Description of the Related Art

Substrate processing apparatuses are known that have a chamber in which a wafer as a substrate is housed, and an exhaust pipe through which particles and gas are exhausted out of the chamber. In this substrate processing apparatus, a wafer housed in the chamber is subjected to desired processing such as etching processing or CVD (chemical vapor deposition) processing, but while the processing is being repeated, particles resulting from reaction product or deposit are produced in the chamber. As the number of particles in the chamber increases, the number of particles that become attached to wafers increases, resulting in the yield of semiconductor devices manufactured from the wafers decreasing. It is thus necessary to detect particles in the chamber on a regular basis.

As a method of detecting particles in the chamber, there is known a method in which the number of particles flowing in the exhaust pipe is detected, and the number and sizes of particles in the chamber are estimated from the detection result. In this detection method, an ISPM (In Situ Particle Monitor) using scattered light is typically used. As the ISPM, there is known an ISPM that has a laser diode that irradiates a laser beam toward particles, and a CCD light-receiving element that receives scattered light produced at this time, so that the sizes and the like of particles are found based on the amount of the received scattered light (see, for example, Japanese Laid-Open Patent Publication (Kokai) No. H05-206235). In this ISPM, scattered light is produced in all directions from a particle, but because the CCD light-receiving element does not face the entire surface of the particle, the CCD light-receiving element can receive only a one-direction component of the scattered light produced in all directions from the particle.

On the other hand, in recent years, as semiconductor devices manufactured from wafers have become miniaturized, the width of trenches and the diameter of via holes formed on wafers have decreased to about several tens of nanometers. Moreover, an interlayer film of a semiconductor device has been required to be made thinner. For this reason, the size of particles that should be detected in a chamber of a substrate processing apparatus is now about several tens of nanometers.

However, because the conventional ISPMs using scattered light merely receive a one-direction component of scattered light produced in all directions from a particle as described above, it is impossible to detect the particle unless it is a very large particle that can produce a large amount of scattered light. For example, the lower limit size of a particle that can be detected is 200 nm. Namely, the conventional ISPMs using scattered light cannot detect fine particles which are several tens of nanometers in size.

SUMMARY OF THE INVENTION

The present invention provides a particle monitor system and a substrate processing apparatus that can detect fine particles.

Accordingly, in a first aspect of the present invention, there is provided a particle monitor system that detects particles in a substrate processing apparatus having a housing chamber in which a substrate is housed and subjected to processing, an exhausting device that exhausts gas out of the housing chamber, and an exhaust pipe that communicates the housing chamber and the exhausting device together, comprising a laser light irradiating device that irradiates laser light toward a space in which the particles may be present and a laser light measurement device that is disposed on an optical path of the laser light having passed through the space and measures energy of the laser light.

According to the first aspect of the present invention, because the laser light measurement device is disposed on an optical path of laser light having passed through a space where particles may be present, the laser light having passed through the space is received by the laser light measurement device. When no particle is present in the space, and thus laser light does not intersect any particle, the energy of the laser light hardly lowers. On the other hand, when a particle is present in the space, and thus laser light intersects the particle, the particle scatters the laser light to disperse the energy thereof and absorbs the energy of the laser light, and hence the energy of the laser light significantly decreases after intersecting the particle. Thus, there is a distinct difference between the energy of laser light when the laser light does not intersect any particle and the energy of laser light when the laser light intersects a particle. For this reason, even when a particle is fine, and thus the amount of scattered laser light and the amount of absorbed laser light are small, the above-mentioned difference is distinct. As a result, by measuring the energy of laser light having passed through the space and observing a difference in energy, a fine particle can be detected.

The present invention can provide a particle monitor system comprising a plurality of reflecting devices that reflect the laser light so that a plurality of optical paths of the laser light lie in the space.

According to the first aspect of the present invention, because laser light is reflected by the plurality of reflecting devices so that a plurality of optical paths of the laser light lie in the space, the probability that particles present in the space will intersect the laser light can be increased without scanning the space with laser light using a moving mirror, and hence the probability that the particles will be detected can be increased, and cost reduction and reliability improvement can be realized.

The present invention can provide a particle monitor system, wherein the laser light irradiating device and the space do not face each other, and the particle monitor system comprises a plurality of reflecting devices that reflect laser light irradiated from the laser light irradiating device so that the laser light enters the laser light measurement device via the space.

According to the first aspect of the present invention, because laser light irradiated from the laser light irradiating device is reflected by the plurality of reflecting devices so that the laser light enters the laser light measurement device via the space that does not face the laser light irradiating device, particles present in the space that does not face the laser light irradiating device can be detected.

The present invention can provide a particle monitor system, wherein the laser light irradiating device irradiates belt-like laser light, and the belt-like laser light covers a cross-section of the space.

According to the first aspect of the present invention, because belt-like laser light irradiated from the laser light irradiating device covers the cross-section of the space where particles may be present, particles can be made to intersect the laser light without scanning the space with laser light using a moving mirror, and hence the probability that the particles will be detected can be reliably increased, and cost reduction and reliability improvement can be realized.

The present invention can a provide particle monitor system, wherein the space to which the laser light is irradiated is a space in the exhaust pipe.

According to the first aspect of the present invention, because the space to which laser light is irradiated is a space in the exhaust pipe, fine particles present in the space in the exhaust pipe can be detected.

The present invention can provide a particle monitor system, wherein the space to which the laser light is irradiated is a space in the housing chamber.

According to the first aspect of the present invention, because the space where particles may be present is a space in the chamber, fine particles present in the space in the chamber can be detected.

Accordingly, in a second aspect of the present invention, there is provided a substrate processing apparatus comprising a housing chamber in which a substrate is housed and subjected to processing, an exhausting device that exhausts gas out of said housing chamber, an exhaust pipe that communicates said housing chamber and said exhausting device together, a laser light irradiating device that irradiates laser light toward a space in which particles may be present, and a laser light measurement device that is disposed on an optical path of the laser light having passed through the space and measures energy of the laser light.

The features and advantages of the invention will become more apparent from the following detailed description taken in conjunction with the accompanying drawings.

DETAILED DESCRIPTION OF THE PREFERRED EMBODIMENTS

Embodiments of the present invention will be described in detail below with reference to the drawings.

First, a description will be given of a substrate processing apparatus and a particle monitor system according to a first embodiment of the present invention.

Figure 1:
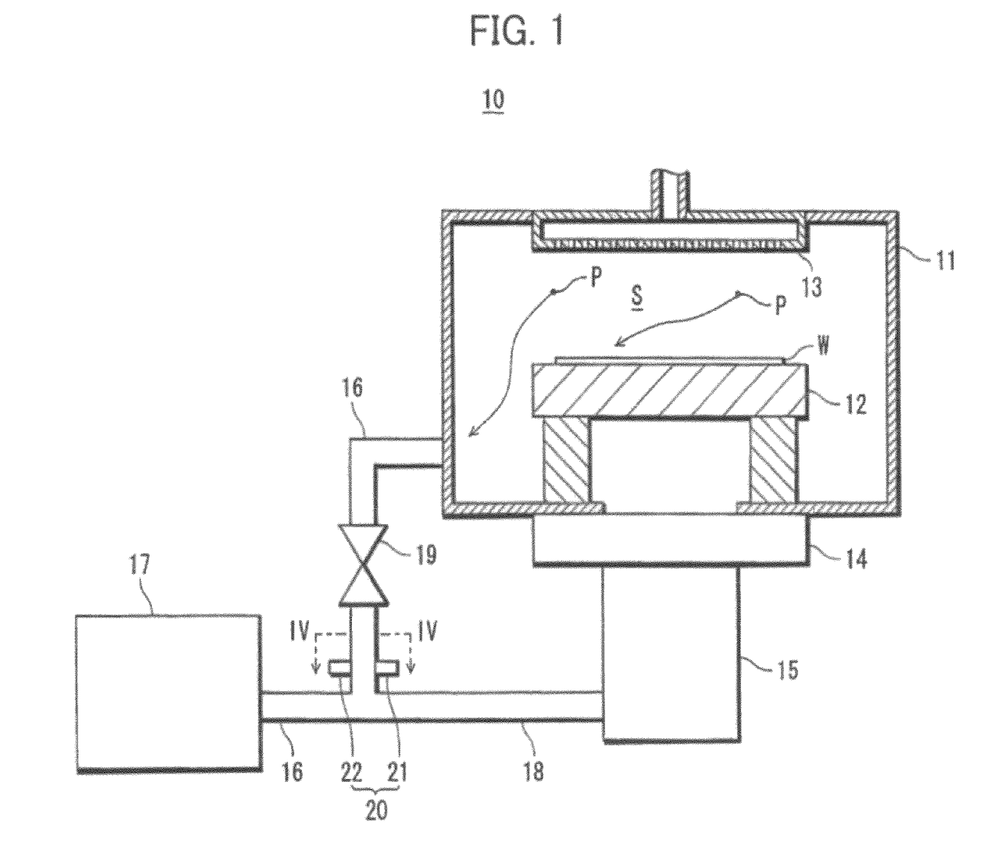
FIG. 1 is a sectional view schematically showing the construction of a substrate processing apparatus according to a first embodiment of the present invention.

FIG. 1 is a sectional view schematically showing the construction of a substrate processing apparatus according to the first embodiment.

As shown FIG. 1, the substrate processing apparatus 10 has a chamber 11 (housing chamber) in which a semiconductor wafer (hereinafter merely referred to as a "wafer") W having a diameter of, for example, 300 mm is housed. In a lower portion of the chamber 11, a stage-shaped lower electrode 12 is disposed, and in an upper portion of the chamber 11, an upper electrode 13 is disposed such as to face the lower electrode 12.

The lower electrode 12 and the upper electrode 13 apply radio frequency electrical power into a processing space S between the lower electrode 12 and the upper electrode 13. The lower electrode 12 also serves as a mounting stage on which the wafer W housed in the chamber 11 is mounted, and the upper electrode 13 also serves as a shower head that supplies a processing gas or the like into the processing space S.

In the chamber 11, the processing gas supplied into the processing space S is turned into plasma through the radio frequency electrical power, and the wafer W is subjected to CVD processing by the plasma. In the substrate processing apparatus 10, while the CVD processing is being repeated, particles resulting from reaction product or deposit are produced in the chamber 11.

The chamber 11 communicates with a TMP (turbo-molecular pump) 15 via an APC (adaptive pressure control) valve 14 and also communicates with a DP (dry pump) 17 (exhausting device) via a cylindrical bypass line 16 (exhaust pipe). The TMP 15 communicates with the bypass line 16 via a main line 18. A valve 19 is disposed part way along the bypass line 16. The APC valve 14 controls the pressure in the chamber 11, and the valve 19 opens and closes the bypass line 16.

The DP 17 exhausts gas and particles out of the chamber 11 via the bypass line 16. The DP 17 also reduces the pressure in the chamber 11 from atmospheric pressure down to a low vacuum state, and the TMP 15 operates in collaboration with the DP 17 to reduce the pressure in the chamber 11 down to a high vacuum state (e.g. a pressure of not more than 133 Pa (1 Torr)), which is at a lower pressure than the low vacuum state.

In the bypass line 16, an ISPM 20 is disposed between the valve 19 and the DP 17. The ISPM 20 has a laser light oscillator 21 (laser light irradiating device) that irradiates laser light toward a space in the bypass line 16 (a space in which particles may be present), and a laser power measurement device 22 (laser light measurement device) disposed on an optical path of the laser light that has been irradiated from the laser light oscillator 21 and passed through the space in the bypass line 16. The laser power measurement device 22 measures the energy of the laser light having passed through the space in the bypass line 16. The measured energy is converted into an electric signal and transmitted to a PC (not shown).

The PC detects the number and sizes of particles flowing in the bypass line 16 based on the transmitted electric signal.

In the substrate processing apparatus 10, when estimating the number and sizes of particles in the chamber 11 using the ISPM 20, the APC valve 14 is closed and the valve 19 is opened so that, first, the pressure in the chamber 11 is reduced by the DP 17, while a large amount of $N_2$ gas or dry air is introduced from the upper electrode 13 into the chamber 11 so as to maintain the pressure in the chamber 11 at 133 Pa (1 Torr). When the pressure is not less than 133 Pa, viscous force of the $N_2$ gas or the like acts on particles in the chamber 11, and the $N_2$ gas or the like is drawn into the bypass line 16 in a state with the particles being caught in the $N_2$ gas or the like, causing the particles in the chamber 11 to flow in the bypass line 16. The ISPM 20 detects the number and sizes of the particles flowing in the bypass line 16.

Figure 2:
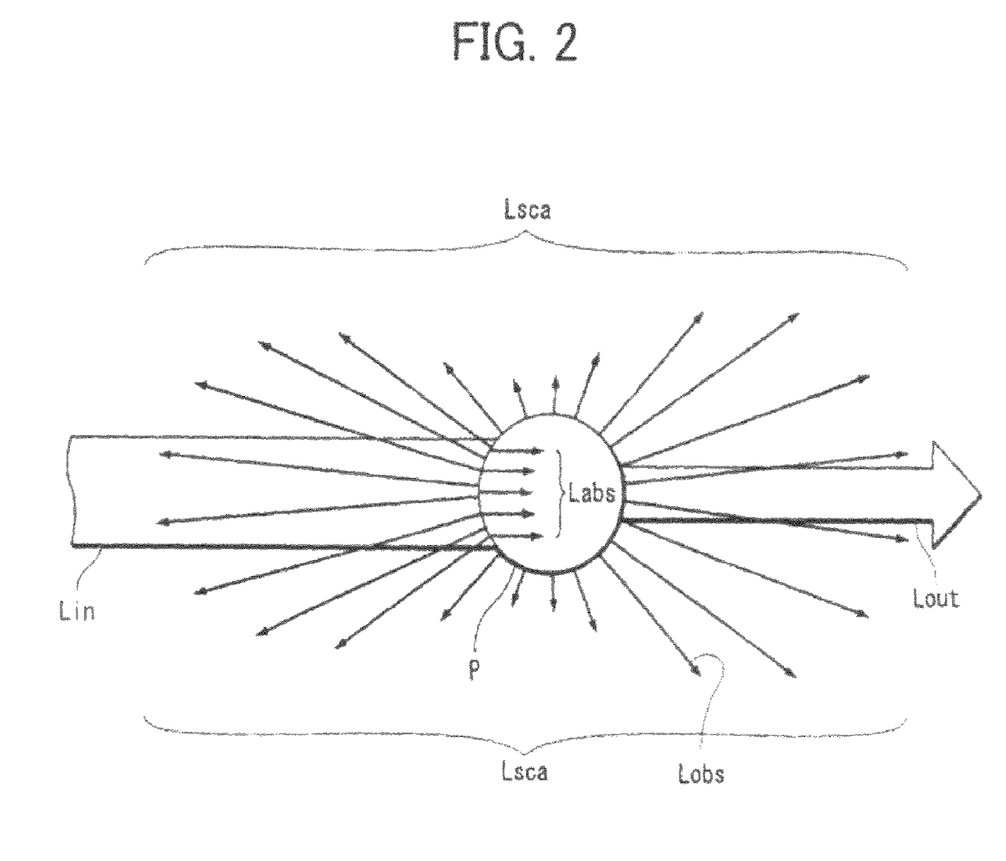
FIG. 2 is a schematic diagram showing how laser light is scattered and absorbed when a particle and the laser light intersect each other.

FIG. 2 is a schematic diagram showing how laser light is scattered and absorbed when a particle and the laser light intersect each other.

As shown in FIG. 2, when a particle P present in the space in the bypass line 16 intersects incident laser light Lin irradiated from the laser light oscillator 21, the particle P scatters a part of the incident laser light Lin in all directions from the particle P and absorbs a part of the incident laser light Lin. In FIG. 2, the scattered laser light is designated by Lsca, and the absorbed laser light is designated by Labs. On the other hand, post-intersection laser light Lout, which is laser light after the incident laser light Lin intersects the particle P and a part thereof is scattered and absorbed, goes in a straight line along an extension of an optical path of the incident laser light Lin.

In the conventional ISPMs using scattered light, because a CCD light receiving element faces a particle P from only one direction, the CCD light receiving element can receive (observe) only observed laser light Lobs, which is a one-direction component of the scattered laser light: Lsca. Therefore, the energy of the observed laser light: Lobs received by the CCD light receiving element is much lower than that of the incident laser light Lin. Thus, when a particle P which the incident laser light Lin intersects is fine, and the amount of the scattered laser light Lsca is small, the energy of the observed laser light Lobs received by the CCD light receiving element is nearly zero. As a result, the conventional ISPMs using scattered light cannot detect fine particles P.

To cope with this, in the present embodiment, post-intersection laser light Lout is observed without observing observed laser light Lobs, which is a one-direction component of scattered laser light Lsca. The energy of the post-intersection laser light Lout never becomes zero unless the entire incident laser light Lin is blocked, and hence the energy of the post-intersection laser light Lout is higher by far than that of the observed laser light Lobs. Moreover, the post-intersection laser light Lout is obtained by removing the scattered laser light Lsca and the absorbed laser light Labs from the incident laser light Lin, and the energy of the scattered laser light Lsca and the absorbed laser light. Labs is higher than that of the observed laser light. Lobs, and hence there is a great difference between the energy of the incident laser light Lin and the energy of the post-intersection laser light Lout. Thus, even when a particle P which the incident laser light Lin intersects is fine, and the energy of the scattered laser light Lsca and the energy of the absorbed laser light Labs are low, there is a distinct difference between the energy of the incident laser light Lin and the post-intersection laser light Lout.

The following relational expressions (1), (2), and (3) show the relationships in energy between laser light:

$$Eout = Ein - Esca - Eabs \qquad \ldots (1)$$

$$Eout > Eobs \qquad \ldots (2)$$

$$Eobs = Esca \times \alpha (\alpha < 1) \qquad \ldots (3)$$

where the energy of incident laser light Lin is represented by Ein, the energy of scattered laser light Lsca is represented by Esca, the energy of absorbed laser light. Labs is represented by Eabs, the energy of observed laser light Lobs is represented by Eobs, and the energy of post-intersection laser light Lout is represented by Eout. On the other hand, when a particle P present in the space in the bypass line 16 does not intersect the incident laser light Lin irradiated from the laser light oscillator 21, the laser power measurement device 22 measures the energy of the incident laser light Lin.

The energy measured when a particle P present in the space in the bypass line 16 intersects the incident laser light Lin is the energy of the post-intersection laser light Lout, the energy measured when the particle P present in the space in the bypass line 16 does not intersect the incident laser light Lin is the energy of the incident light Lin, and there is a distinct difference between the energy of the incident laser light Lin and the energy of the post-intersection laser light Lout. Therefore, by measuring the energy of laser light L having passed through the space in the bypass line 16 and observing differences in energy using the laser power measurement device 22, fine particles P present in the space in the bypass line 16 can be detected.

Figure 3:
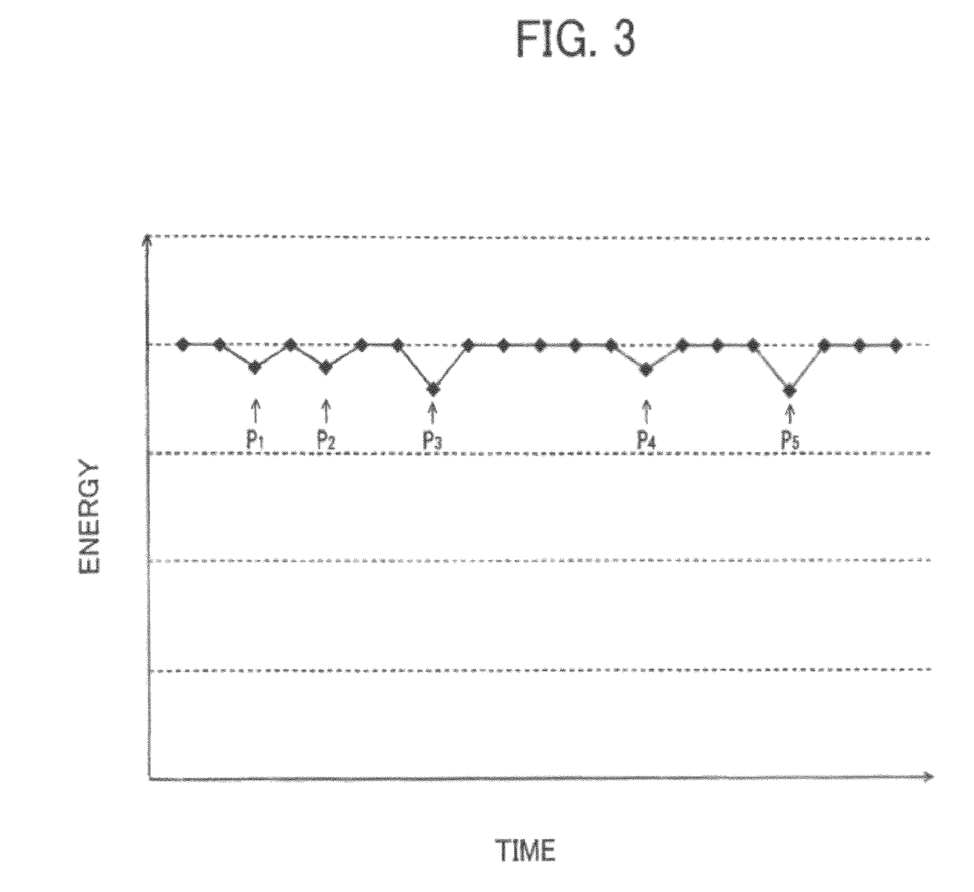
FIG. 3 is a graph showing an example of results obtained by measurements on the energy of laser light according to the first embodiment.

FIG. 3 is a graph showing an example of results obtained by measurements on the energy of laser light according to the present embodiment.

As shown by the graph of FIG. 3, the energy of measured laser light L distinctly decreases at observation points P1 to P5 at which fine particles P intersect incident laser light Lin, and hence it was found that fine particles P can be detected by measuring the energy of the laser light L.

Moreover, in the conventional ISPMs using scattered light, because laser light is merely irradiated toward a space in which particles may be present, only one optical path of the laser light lies in the space. Further, because the width of laser light irradiated from a laser diode is small, the probability that particles present in the space will intersect the optical path of the laser light is low, and also, the focus of a detection system is small. Thus, the probability that particles will be detected is low.

To cope with this, there has been proposed a method in which laser light is caused to scan the space using a moving mirror so as to increase the probability that particles will intersect an optical path of the laser light. However, because there is a limit on the scanning speed of the laser light, particles moving at high speed often pass through the space without intersecting the laser light. Moreover, because the moving mirror has a moving part, the moving mirror easily breaks down, which increases system cost and decreases reliability.

To cope with this, in the present embodiment, the probability that particles will intersect an optical path of laser light is increased without using the moving mirror.

Figure 4:
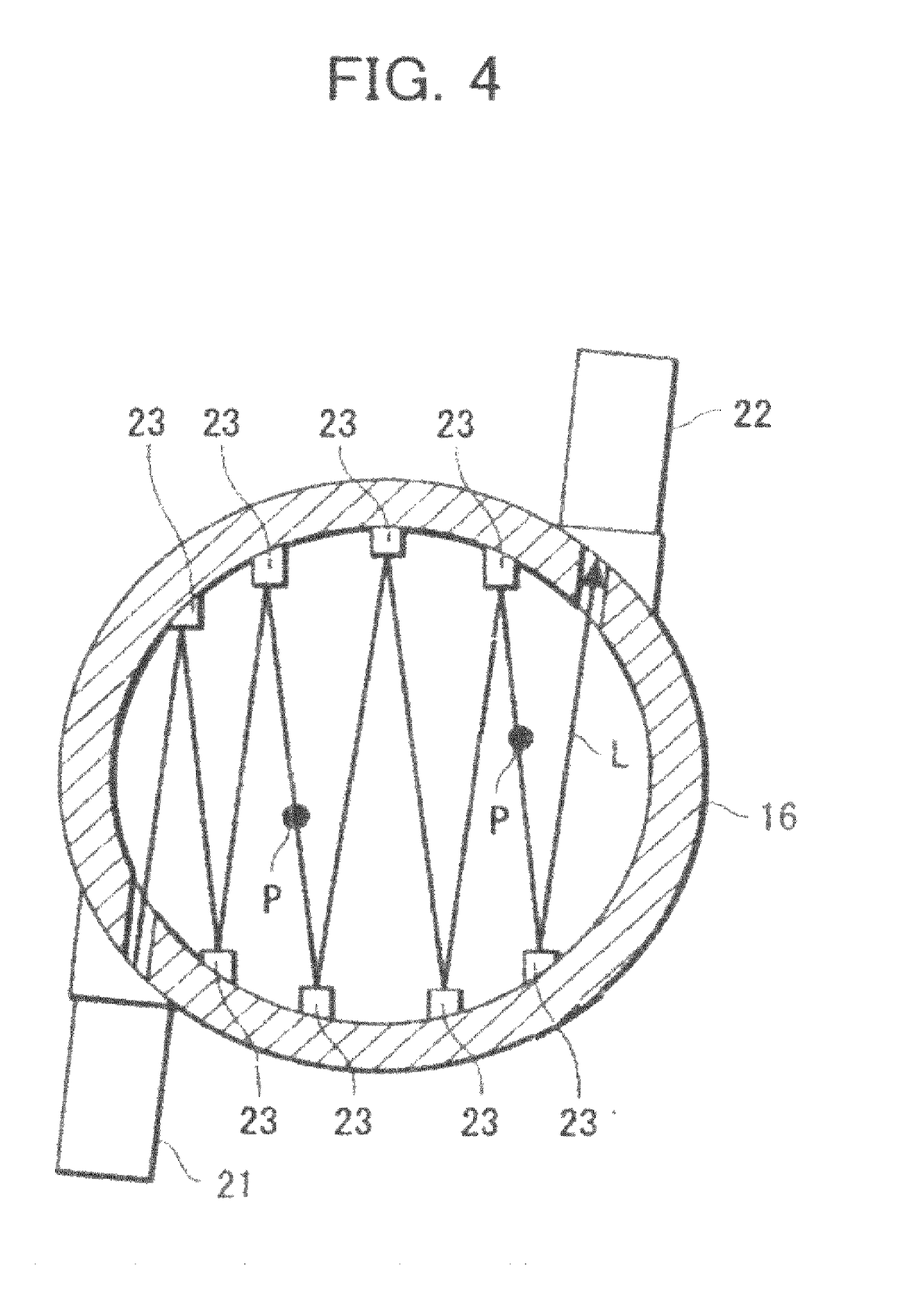
FIG. 4 is a sectional view taken along line IV-IV of FIG. 1.

FIG. 4 is a sectional view taken along line IV-IV of FIG. 1.

As shown in FIG. 4, a plurality of laser reflecting mirrors 23 (reflecting devices) are disposed on an inside wall of the bypass line 16. Each laser reflecting mirror 23 reflects incident laser light L toward another laser reflecting mirror 23. At least one of the plurality of laser reflecting mirrors 23 faces the laser light oscillator 21, and at least another one of plurality of the laser reflecting mirrors 23 faces the laser power measurement device 22.

Because laser light L irradiated from the laser light oscillator 21 is reflected by the plurality of laser reflecting mirrors 23 in the bypass line 16, at least two optical paths of the laser light L lie in the space in the bypass line 16, whereby the probability that particles P present in the space in the bypass line 16 will intersect the laser light L can be increased. Moreover, because at least one laser reflecting mirror 23 faces the laser power measurement device 22, the laser light L reflected by the plurality of laser reflecting mirrors 23 is finally received by the laser power measurement device 22. Thus, the laser power measurement device 22 is disposed on the optical path of the laser light L having passed through the space in the bypass line 16.

It should be noted that in the present embodiment, the laser light oscillator 21, the laser power measurement device 22, and the plurality of laser reflecting mirrors 23 constitute a particle monitor system.

According to the substrate processing apparatus and the particle monitor system of the present embodiment, because the laser power measurement device 22 is disposed on an optical path of laser light L having passed through the space in the bypass line 16, the laser light L having passed through the space in the bypass line 16 is received by the laser power measurement device 22 so that the energy thereof is measured. Here, the energy measured when no particle P is present in the space in the bypass line 16 and the laser light L does not intersect any particle P is the energy of the incident laser light Lin, while the energy measured when a particle P is present in the space in the bypass line 16 and the laser light L intersects the particle P is the energy of post-intersection laser light Lout. As described above, even when a particle P is fine, and the energy of scattered laser light Lsca and the energy of absorbed laser light Labs are low, there is a distinct difference between the energy of the incident laser light Lin and the energy of the post-intersection laser light Lout. Therefore, by measuring the energy of the laser light L having passed through the space in the bypass line 16 and observing differences in energy, fine particles P present in the space in the bypass line 16 can be detected.

In the substrate processing apparatus 10 described above, because laser light L is reflected on the plurality of laser reflecting mirrors 23 so that at least two optical paths of the laser light L lie in the space in the bypass line 16, the probability that particles P present in the space in the bypass line 16 will intersect the laser light L can be increased, and hence the probability that the particles P will be detected can be increased. Moreover, the space in the bypass line 16 does not have to be scanned with laser light L using a moving mirror, cost reduction and reliability improvement of the substrate processing apparatus 10 and the particle monitor system can be realized, and furthermore, the probability that particles P moving at high speed will intersect laser light L can be increased.

It should be noted that in the substrate processing apparatus 10 described above, when laser light L is to be reflected on the plurality of laser reflecting mirrors 23, in a case where two optical paths of the laser light L lying in the space in the bypass line 16 intersect each other, and a particle P is present at the point of intersection, the laser light L is scattered twice and the energy thereof is absorbed twice by the same particle P, and hence the effect of the particle P is reflected on post-intersection laser light Lout twice. It is thus preferred that laser light L is reflected on the plurality of laser reflecting mirrors 23 in such a manner that two or more optical paths of the laser light L lying in the space in the bypass line 16 do not intersect each other.

In the substrate processing apparatus 10 described above, there is no limit on the type and wavelength of laser light oscillated by the laser light oscillator 21. Moreover, there is no limit on the material of the laser reflecting mirrors 23, but it is preferred that the laser reflecting mirrors 23 are made of a material whose reflection efficiency is not decreased by plasma or the like entering the bypass line 16, for example, a material resistant to plasma.

Next, a description will be given of a substrate processing apparatus and a particle monitor system according to a second embodiment of the present invention.

The present embodiment is basically the same as the first embodiment described above in terms of construction and operation, differing from the first embodiment in the construction of the particle monitor system. Features of the construction and operation that are the same as in the first embodiment will thus not be described, only features that are different from those of the first embodiment being described below.

In the conventional ISPMs using scattered light, because laser light is directly irradiated from a laser diode toward a space where particles may be present, it is impossible to detect particles present in a space that does not face the laser diode. To cope with this, the present embodiment provides a construction described below.

Figure 5:
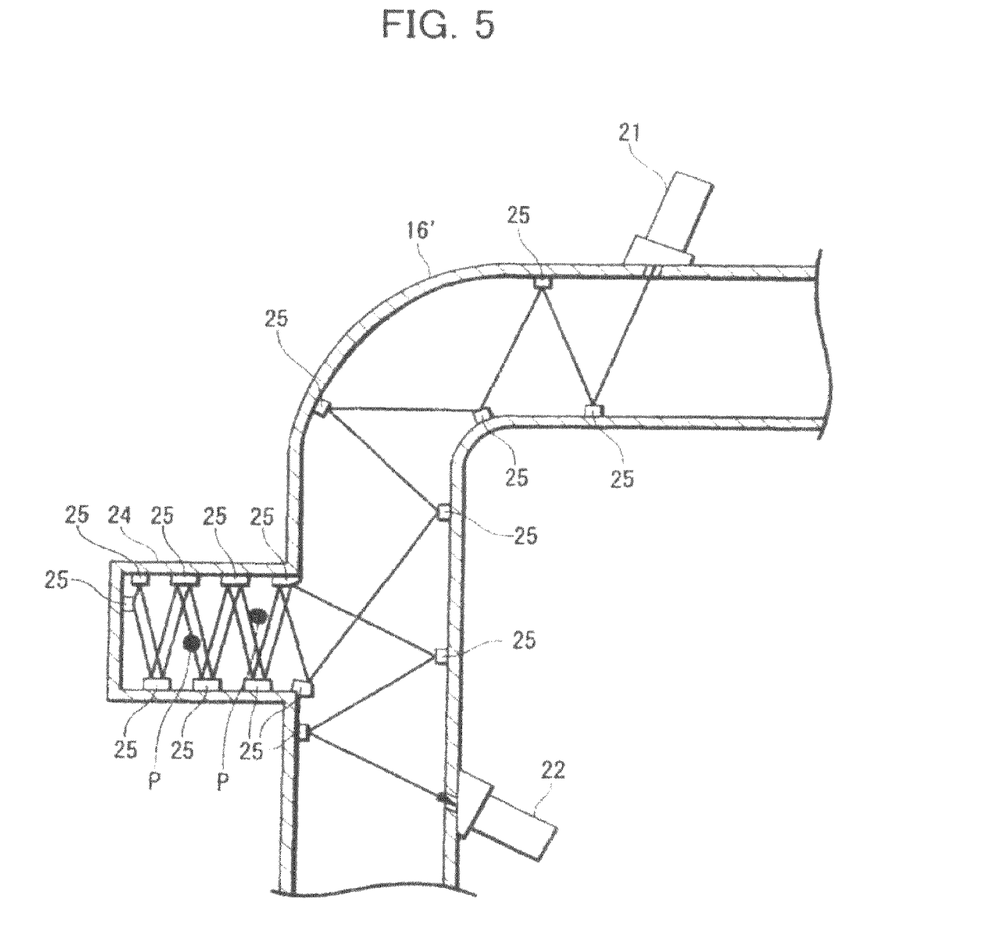
FIG. 5 is a sectional view schematically showing how a plurality of laser reflection mirrors are arranged according to a second embodiment of the present invention.

FIG. 5 is a sectional view schematically showing how a plurality of laser reflecting mirrors are arranged according to the present embodiment.

As shown in FIG. 5, a bypass line 16' has a concave portion 24 that does not face the laser light oscillator 21, and a plurality of laser reflecting mirrors 25 (reflecting devices) are disposed on an inside wall of the bypass line 16' and an inside wall of the concave portion 24. The laser light oscillator 21 and the laser power measurement device 22 are disposed at such locations as not to face the concave portion 24. Each laser reflecting mirror 25 reflects incident laser light toward another laser reflecting mirror 25.

At least one of the plurality of laser reflecting mirrors 25 faces the laser light oscillator 21, and at least another one of the plurality of laser reflecting mirrors 25 faces the laser power measurement device 22. Moreover, some of the plurality of laser reflecting mirrors 25 disposed on the inside wall of the bypass line 16' reflect laser light L incident from the laser light oscillator 21 and guide the laser light L into a space in the concave portion 24. The plurality of laser reflecting mirrors 25 disposed on the inside wall of the concave portion 24 reflect the laser light L guided into the space in the concave portion 24 so that at least two optical paths of the laser light L lie in the space in the concave portion 24, and the laser light L finally exits the space in the concave portion 24. The rest of the plurality of laser reflecting mirrors 25 disposed on the inside wall of the bypass line 16'reflects the laser light L so that the laser light L having exited the space in the concave portion 24 enters the laser power measurement device 22.

It should be noted that in the present embodiment, the laser light oscillator 21, the laser power measurement device 22, and the plurality of laser reflecting mirrors 25 constitute the particle monitor system.

According to the substrate processing apparatus and the particle monitor system of the present embodiment, because laser light L irradiated from the laser light oscillator 21 is reflected by the plurality of laser reflecting mirrors 25 so that the laser light L enters the :Laser power measurement device 22 via the space in the concave portion 24, particles present in the space in the concave portion 24 can be detected.

Moreover, in the substrate processing apparatus described above, because laser light L is reflected so that at least two optical paths of the laser light L lie in the space in the concave portion 24, the probability that particles P present in the space in the concave portion 24 will intersect the laser light L can be increased.

Next, a description will be given of a substrate processing apparatus and a particle monitor system according to a third embodiment of the present invention.

The present embodiment is basically the same as the first embodiment described above in terms of construction and operation, differing from the first embodiment in the construction of the particle monitor system. Features of the construction and operation that are the same as in the first embodiment will thus not be described, only features that are different from those of the first embodiment being described below.

Figure 6:
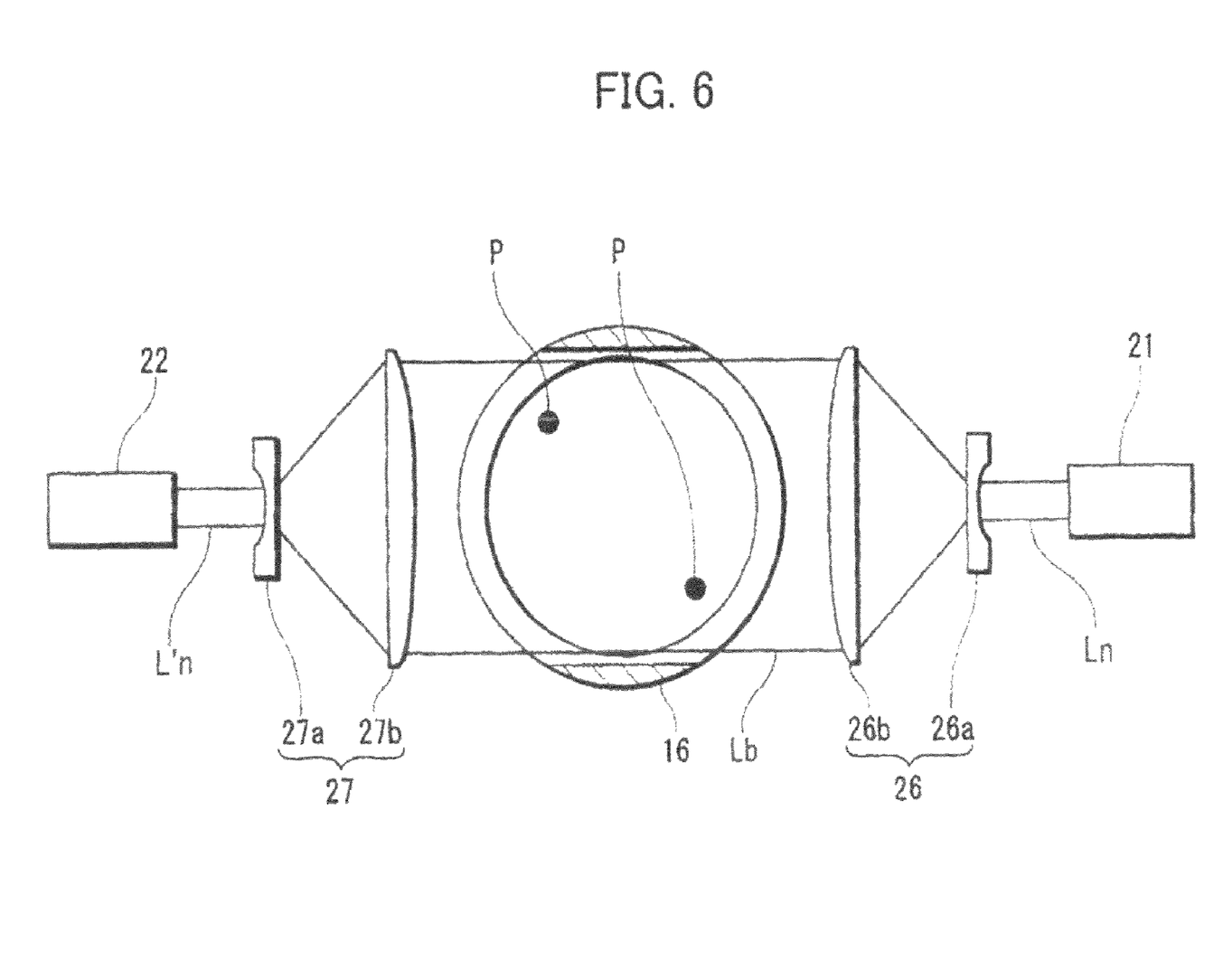
FIG. 6 is a sectional view schematically showing the construction of a particle monitor system according to a third embodiment of the present invention.

FIG. 6 is a sectional view schematically showing the construction of the particle monitor system according to the present embodiment. The position of the cross-section in FIG. 6 in the substrate processing apparatus is the same as that of the cross-section in FIG. 4.

As shown in FIG. 6, an incidence optical system 26 comprised of a concave lens 26a and a convex lens 26b is disposed between the laser light oscillator 21 and the bypass line 16, and an emission optical system 27 comprised of a concave lens 27a and a convex lens 27b is disposed between the bypass line 16 and the laser power measurement device 22. The incidence optical system 26 increases the width of linear laser light Ln irradiated by the laser light oscillator 21 into a belt form and emits belt-like laser light Lb toward a space in the bypass line 16, and the emission optical system 27 reduces the width of the belt-like laser light Lb having passed through the space in the bypass line 16 into a linear form and emits linear laser light L'n toward the laser power measurement device 22.

In the present embodiment, the width of belt-like laser light Lb emitted by the incidence optical system 26 is set to be substantially the same as the inner diameter of the bypass line 16, and hence the belt-like laser light Lb covers substantially the entire cross-section of the space in the bypass line 16. Therefore, particles P present in the space in the bypass line 16 intersect the belt-like laser light Lb.

It should be noted that in the present embodiment, the laser light oscillator 21, the laser power measurement device 22, the incidence optical system 26, and the emission optical system 27 constitute the particle monitor system.

According to the substrate processing apparatus and the particle monitor system of the present embodiment, because belt-like laser light Lb irradiated from the laser light oscillator 21 and widened by the incidence optical system 26 covers substantially the entire cross-section of the space in the bypass line 16, particles P present in the space in the bypass line 16 can be made to intersect the belt-like laser light Lb even if the particles P are moving at high speed, and hence the probability that the particles P will be detected can be reliably increased. Moreover, because the space in the bypass line 16 does not have to be scanned with laser light L using a moving mirror, cost reduction and reliability improvement of the substrate processing apparatus and the particle monitor system can be realized.

Figure 7:
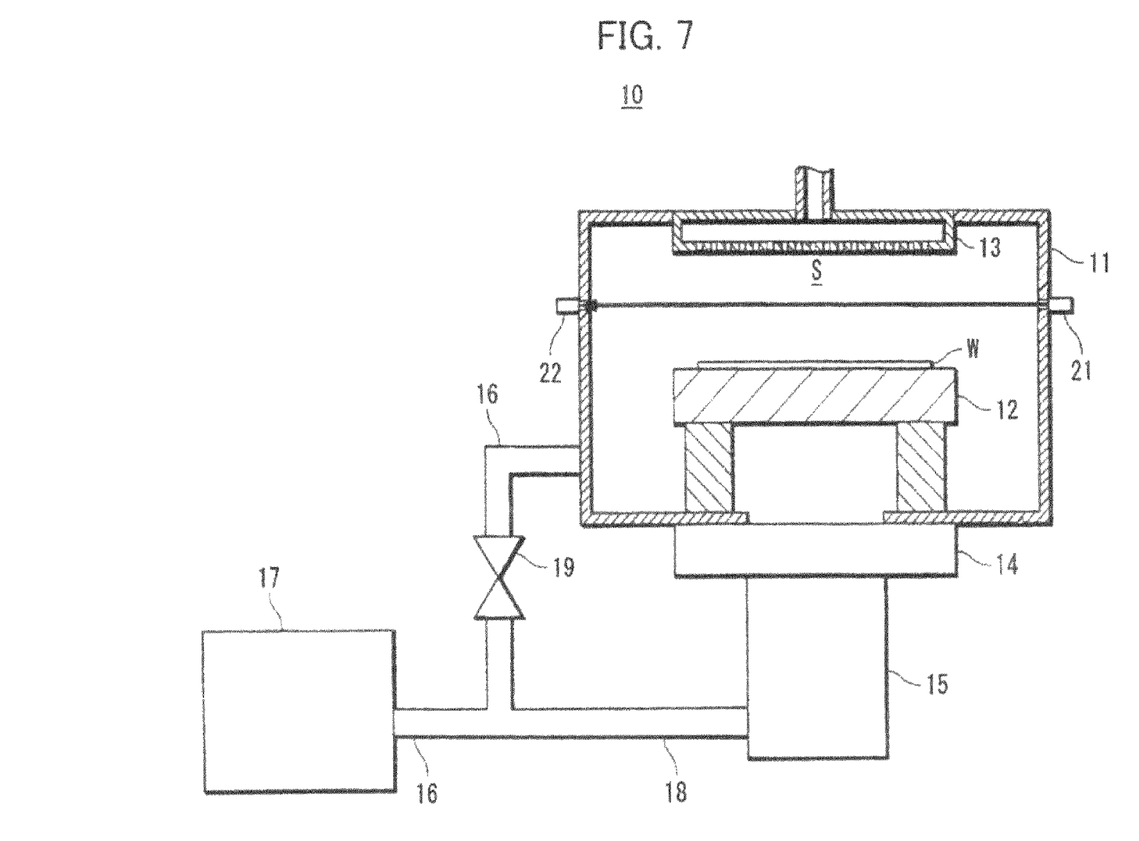
FIG. 7 is a sectional view schematically showing the construction of a substrate processing apparatus having a particle monitor system that detects particles in a space of a chamber.

Although in the above described embodiments, the ISPM 20 is provided in the bypass line 16 so as to detect particles P present in the space in the bypass line 16, the laser light oscillator 21 and the laser power measurement device 22 may be provided in a side wall of the chamber 11 as shown in FIG. 7 so as to detect particles P present in a space (in particular, the processing space S) in the chamber 11.

Moreover, the particle monitor systems according to the above described embodiments may be used to detect not only particles present in the space in the bypass line 16 or the space in the chamber 11 in pressure-reduced atmosphere, but also particles in an atmosphere at atmospheric pressure, for example, particles in a clean room and a loader module as a substrate transfer apparatus.

Further, although in the particle monitor systems according to the above described embodiments, the laser power measurement device 22 measures the energy of laser light L having passed through the space in the bypass line 16 or the space in the concave portion 24 to merely observe differences in energy, observed laser light Lobs as one-direction components of scattered laser light Lsca produced through intersection of laser light L and particles P may be additionally observed if possible, and the particles P may be detected based on energy differences and scattering of the laser light L, so that detection sensitivity can be further increased.

It should be noted in the above described embodiments, the substrates subjected to the CVD processing by the substrate processing apparatus are not limited to being semiconductor wafers W, but rather may instead be glass substrates used in LCDs (Liquid Crystal Displays), FPDs (Flat Panel Displays) or the like. Moreover, the processing to which the substrate are subjected by the substrate processing apparatus is not limited to being the CVD processing, but rather may instead be etching processing or the like.

What is claimed is:

1. A particle monitor system that detects particles in an exhaust pipe of a substrate processing apparatus having a housing chamber in which a substrate is housed and subjected to processing, an exhausting device that exhausts gas out of the housing chamber, and the exhaust pipe that communicates the housing chamber and the exhausting device together, the particle monitor system comprising:
    a laser light irradiating device that is disposed on the exhaust pipe and irradiates laser light toward a space in the exhaust pipe into which the particles flow; and
    a laser light measurement device that is disposed on an optical path of the laser light having passed through the space in the exhaust pipe and measures energy of the laser light,
    wherein the particle monitor system detects particles that flow into the space based on a difference between an energy of the laser light irradiated from the laser light irradiating device and an energy of the laser light measured by the laser light measurement device.

2. A particle monitor system as claimed in claim 1, comprising a plurality of reflecting devices that reflect the laser light so that a plurality of optical paths of the laser light lie in the space.

3. A particle monitor system as claimed in claim 1, wherein the laser light irradiating device and a sub space included in the space do not face each other, and
    the particle monitor system further comprises a plurality of reflecting devices that reflect the laser light irradiated from the laser light irradiating device so that the laser light enters the laser light measurement device via the sub space.

4. A particle monitor system as claimed in claim 1, wherein the laser light irradiating device irradiates belt-like laser light, and the bell-like laser light covers a cross-section of the space.

5. A particle monitor system as claimed in claim 3, wherein the sub space is a concave portion that is disposed on the exhaust pipe.

6. A particle monitor system as claimed in claim 2, wherein the plurality of reflecting devices are disposed on the exhaust pipe.

7. A particle monitor system as claimed in claim 2, wherein the plurality of reflecting devices reflect the laser light along non-intersecting optical paths.

8. A particle monitor system as claimed in claim 2, wherein at least one of the plurality of reflecting devices faces the laser light irradiating device, at least another one of the plurality of reflecting devices faces the laser light measurement device, and the other reflecting devices do not face horizontally with each other.

9. A particle monitor system that detects particles in a housing chamber of a substrate processing apparatus having the housing chamber in which a substrate is housed and subjected to processing, an exhausting device that exhausts gas out of the housing chamber, and an exhaust pipe that communicates the housing chamber and the exhausting device together, the particle monitor system comprising:
  a laser light irradiating device that is disposed on the housing chamber and irradiates laser light toward a space in the housing chamber into which the particles flow; and
  a laser light measurement device that is disposed on an optical path of the laser light having passed through the space in the housing chamber and measures energy of the laser light,
  wherein the particle monitor system detects particles that flow into the space based on a difference between an energy of the laser light irradiated from the laser light irradiating device and an energy of the laser light measured by the laser light measurement device.

10. A particle monitor system as claimed in claim 9, comprising a plurality of reflecting devices that reflect the laser light so that a plurality of optical paths of the laser light lie in the space.

11. A particle monitor system as claimed in claim 9, wherein the laser light irradiating device and a sub space included in the space do not face each other, and
  the particle monitor system further comprises a plurality of reflecting devices that reflect the laser light irradiated from the laser light irradiating device so that the laser light enters the laser light measurement device via the sub space.

12. A particle monitor system as claimed in claim 9, wherein the laser light irradiating device irradiates belt-like laser light, and the belt-like laser light covers a cross-section of the space.

13. A particle monitor system as claimed in claim 11, wherein the sub space is a concave portion that is disposed on the housing chamber.

14. A particle monitor system as claimed in claim 10, wherein the plurality of reflecting devices are disposed on the housing chamber.

15. A particle monitor system as claimed in claim 10, wherein the plurality of reflecting devices reflect the laser light along non-intersecting optical paths.

16. A particle monitor system as claimed in claim 10, wherein at least one of the plurality of reflecting devices faces the laser light irradiating device, at least another one of the plurality of reflecting devices faces the laser light measurement device, and the other reflecting devices do not face horizontally with each other.

* * * * *